United States Patent
Suganuma et al.

(10) Patent No.: US 10,702,606 B2
(45) Date of Patent: Jul. 7, 2020

(54) PEPTIDE COMPOSITION

(71) Applicant: MENICON CO., LTD., Nagoya-shi, Aichi (JP)

(72) Inventors: Yuya Suganuma, Kasugai (JP); Tatsuya Ojio, Kasugai (JP); Hidenori Yokoi, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 0 days.

(21) Appl. No.: 15/780,686

(22) PCT Filed: Dec. 10, 2015

(86) PCT No.: PCT/JP2015/084638
§ 371 (c)(1),
(2) Date: Jun. 1, 2018

(87) PCT Pub. No.: WO2017/098627
PCT Pub. Date: Jun. 15, 2017

(65) Prior Publication Data
US 2018/0344861 A1    Dec. 6, 2018

(51) Int. Cl.
| | |
|---|---|
| A61K 47/42 | (2017.01) |
| A61K 9/08 | (2006.01) |
| A61L 27/00 | (2006.01) |
| A61L 27/22 | (2006.01) |
| A61L 27/52 | (2006.01) |
| C07K 7/08 | (2006.01) |

(52) U.S. Cl.
CPC ............ *A61K 47/42* (2013.01); *A61K 9/08* (2013.01); *A61L 27/00* (2013.01); *A61L 27/22* (2013.01); *A61L 27/52* (2013.01); *C07K 7/08* (2013.01); *A61L 2300/412* (2013.01)

(58) Field of Classification Search
CPC .......... A61K 47/42; A61K 9/08; A61K 47/22; A61K 47/183; A61L 2300/412; A61L 27/00; A61L 27/22; A61L 27/52; C07K 7/08
See application file for complete search history.

(56) References Cited

U.S. PATENT DOCUMENTS

| | | | |
|---|---|---|---|
| 5,093,322 A | 3/1992 | Bonin et al. | |
| 5,849,700 A | 12/1998 | Sørensen et al. | |
| 5,849,704 A | 12/1998 | Sørensen et al. | |
| 6,022,858 A | 2/2000 | Sørensen et al. | |
| 7,554,021 B2 * | 6/2009 | Stupp | C07K 7/06 428/113 |
| 8,299,032 B2 * | 10/2012 | Yokoi | C07K 7/08 514/21.4 |
| 8,729,032 B2 * | 5/2014 | Nagai | A61L 15/60 514/21.4 |
| 8,951,974 B2 * | 2/2015 | Nagai | A61L 15/60 514/21.5 |
| 9,012,404 B2 | 4/2015 | Spirio et al. | |
| 2006/0084607 A1 | 4/2006 | Spirio et al. | |
| 2008/0267907 A1 | 10/2008 | Poulsen | |
| 2010/0016548 A1 * | 1/2010 | Yokoi | C07K 7/08 530/326 |
| 2010/0143504 A1 | 6/2010 | Spirio et al. | |
| 2010/0221224 A1 | 9/2010 | Stupp et al. | |
| 2011/0076273 A1 | 3/2011 | Adler et al. | |
| 2012/0058066 A1 | 3/2012 | Nagai et al. | |
| 2013/0281547 A1 | 10/2013 | Spirio et al. | |
| 2014/0161753 A1 | 6/2014 | Nagai et al. | |
| 2014/0286888 A1 | 9/2014 | Nagai et al. | |
| 2015/0086537 A1 | 3/2015 | Adler et al. | |
| 2015/0125611 A1 | 5/2015 | Nagai et al. | |
| 2015/0258166 A1 | 9/2015 | Spirio et al. | |
| 2015/0315242 A1 | 11/2015 | Nagai et al. | |
| 2016/0137742 A1 | 5/2016 | Adler et al. | |
| 2016/0317607 A1 | 11/2016 | Spirio et al. | |

FOREIGN PATENT DOCUMENTS

| | | |
|---|---|---|
| JP | H11-315031 A | 11/1999 |
| JP | 2008-505919 A | 2/2008 |
| JP | 4620804 B2 | 1/2011 |
| JP | 5558104 B2 | 7/2014 |
| JP | 2014-214153 A | 11/2014 |
| JP | 2015-061839 A | 4/2015 |
| JP | 2015-144767 A | 8/2015 |
| WO | 93/12812 A1 | 7/1993 |
| WO | 2006/014570 A2 | 2/2006 |
| WO | 2010/103887 A1 | 9/2010 |
| WO | 2011/029892 A2 | 3/2011 |
| WO | 2013/123432 A2 | 8/2013 |
| WO | 2014/178216 A1 | 11/2014 |

OTHER PUBLICATIONS

Important Biological Buffers, accessed online on May 22, 2019 at http://staff.ustc.edu.cn/~liuyz/methods/buffer.htm, 3 pages. (Year: 2019).*
"Buffer pKa and pH Range Values", https://animalscience.unl.edu/Research/RumNut/RumNutLab/99-bufferpkaandphrangevalues%281%29.pdf, accessed online May 22, 2019, 2 pages. (Year: 2019).*
Cerpa et al. Conformational switching in designed peptides: the helix/sheet transition. Folding and Design 1996. vol. 1, p. 91-101. (Year: 1996).*
Important biological buffers, http://staff.ustc.edu.cn/~liuyz/methods/buffer.htm accessed online on Feb. 6, 2020. 2 pages. (Year: 2020).*
Jun. 13, 2019 Extended Search Report issued in European Patent Application No. 15910243.3.
Nagai, Yusuke et al., "The Mechanical Stimulation of Cells in 3D Culture Within a Self-Assembling Peptide Hydrogel", Biomaterials, vol. 33, No. 4, (2012, available 2011), pp. 1044-1051.
Jun. 5, 2019 Office Action issued in Russian Patent Application No. 2018124983/04(039600).
Mar. 1, 2016 International Search Report issued in International Patent Application No. PCT/JP2015/084638.

(Continued)

*Primary Examiner* — Marcela M Cordero Garcia
(74) *Attorney, Agent, or Firm* — Oliff PLC

(57) ABSTRACT

The present invention provides a peptide composition that can achieve both excellent storage stability and transparency. The peptide composition of the present invention includes: a self-assembling peptide; a buffering agent having a pKa of 3.5 or more and less than 7.5 and containing one or more nitrogen atoms; and water, and has a pH of from 4.5 to 6.6.

5 Claims, No Drawings
Specification includes a Sequence Listing.

(56) References Cited

OTHER PUBLICATIONS

Apr. 7, 2020 Office Action issued in Russian Patent Application No. 2018124983/04(039600).
Petrovsky, B.V., "Big Medical Encyclopedia", 1982, T. 19, p. 239.
Petrovsky, B.V., "Big Medical Encyclopedia", 1985, T. 25, pp. 59-60.

* cited by examiner

```
                            SEQUENCE LISTING

<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 1

Arg Leu Asp Leu Arg Leu Ala Leu Arg Leu Asp Leu Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: a self-assembling peptide that can be used in
      the present invention

<400> SEQUENCE: 2

Arg Leu Asp Leu Arg Leu Ser Leu Arg Leu Asp Leu Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: a self-assembling peptide that can be use in
      the present invention

<400> SEQUENCE: 3

Arg Leu Ala Leu Arg Leu Asp Leu Arg Leu Asp Leu Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: a self-assembling peptide that can be use in
      the present invention

<400> SEQUENCE: 4

Lys Arg Leu Asp Leu Asn Leu Arg Leu Asp Leu Arg Lys
1               5                   10
```

PEPTIDE COMPOSITION

TECHNICAL FIELD

The present invention relates to a peptide composition.

BACKGROUND ART

In recent years, a peptide composition has been used in various applications. For example, there is known a peptide gel using a peptide having a self-assembling ability. The peptide gel has excellent mechanical strength and transparency, and hence has been used in various applications (for example, Patent Literature 1).

The peptide composition contains a buffering agent in some cases so as to be adjusted to a pH suited for an application. For example, there is a disclosure that, in preparation of a composition for cardiac tissue protection and regeneration, an acceptable buffer solution may be used to bring the composition to a physiologically acceptable pH (Patent Literature 2).

CITATION LIST

Patent Literature

[PTL 1] JP 4620804 B2
[PTL 2] JP 5558104 B2

SUMMARY OF INVENTION

Technical Problem

However, as a result of an investigation made by the inventors of the present invention, it has been found that the related-art peptide composition has a problem with storage stability in some cases. Specifically, when a peptide composition having its pH adjusted with a buffering agent, such as sodium carbonate, is stored, the pH varies temporally in some cases. It has also been found that, in a peptide composition containing a peptide having its C-terminal carboxyl group amidated, hydrolysis of the amide group occurs along with the pH variation in some cases, and such tendency is strong when an amino acid residue at the C-terminus is a basic amino acid residue.

The amide group may function as a protecting group for the C-terminus of the peptide. When the amide group serving as the protecting group is removed and degraded into a carboxyl group during storage, desired characteristics of the peptide are impaired in some cases. Further, there is also a risk that a by-product produced by the degradation may serve as an impurity to lower the quality of the peptide composition. In addition, the amide group contained in the peptide is an important functional group also from the viewpoints of expressing physiological activity and forming a molecular assembly having a specific structure. Particularly in a peptide having a self-assembling ability (hereinafter referred to as self-assembling peptide), the amide group is a functional group important for forming a molecular assembly, that is, for the self-assembling ability. The number and arrangement of charges in a peptide molecule are associated with the self-assembling ability, and hence, for example, the conversion of the amide group at the C-terminus into a different functional group (e.g., a carboxyl group) may affect the self-assembling ability. Specifically, even when the sequence of the self-assembling peptide is same, whereas a transparent peptide composition is obtained in the case where the C-terminus is an amide group, the transparency of the composition may be impaired in the case where the C-terminus is a carboxylic acid.

The present invention has been made in order to solve the above-mentioned problem, and an object of the present invention is to provide a peptide composition that can achieve both excellent storage stability and characteristics desired of a peptide composition (e.g., transparency).

Solution to Problem

According to one embodiment of the present invention, there is provided a peptide composition. The peptide composition includes: a self-assembling peptide; a buffering agent having a pKa of 3.5 or more and less than 7.5 and containing one or more nitrogen atoms; and water, and has a pH of from 4.5 to 6.6.

In one embodiment, a total charge of amino acid residues contained in the self-assembling peptide is more than 0 and +3 or less in the peptide composition.

In one embodiment, a C-terminus of the self-assembling peptide includes an amide group.

In one embodiment, an amino acid at a C-terminus of the self-assembling peptide includes a basic amino acid.

In one embodiment, the buffering agent includes histidine, thiamine nitrate, pyridine, bis-Tris, ethylenediamine, and/or N-methylmorpholine.

In one embodiment, a concentration of the buffering agent is from 1 mM to 100 mM.

In one embodiment, the peptide composition has a visible light transmittance of 70% or more.

According to another embodiment of the present invention, there is provided a production method for the peptide composition. The production method includes agitating a self-assembling peptide, a buffering agent having a pKa of 3.5 or more and less than 7.5 and containing one or more nitrogen atoms, and water.

Advantageous Effects of Invention

The peptide composition of the present invention contains the self-assembling peptide, the buffering agent having a pKa of 3.5 or more and less than 7.5 and containing one or more nitrogen atoms, and the water, and has a pH of from 4.5 to 6.6. The peptide composition of the present invention can achieve both excellent storage stability and desired characteristics (e.g., transparency). Accordingly, the peptide composition of the present invention can maintain its quality even when stored for a certain period of time, and can be suitably used in various applications.

The reason why the above-mentioned effect is obtained has yet to be elucidated, but is presumably as described below. That is, in the related-art peptide composition, the content of the buffering agent is gradually decreased by vaporization or the like to weaken its buffering action during a storage period. Presumably as a result of this, the pH of the composition changes to cause degradation on the peptide having low pH stability (e.g., degradation of a C-terminal amide group). In contrast, in the present invention, the specific buffering agent is selected, and hence the temporal pH change can be suppressed. As a result, the pH of the composition can be controlled to the specific pH range in which the degradation of the peptide is less liable to occur. Further, the specific buffering agent can also provide, for example, the following effect: characteristics desired of a self-assembling peptide composition (e.g., transparency) can be maintained.

Further, when a buffering agent that is liable to vaporize is used in a peptide composition, there is also a problem in that its preparation at a constant pH is difficult, resulting in a batch-to-batch variation. The use of the above-mentioned buffering agent facilitates the control of the pH of the peptide composition, and hence can suppress the batch-to-batch variation in quality of the peptide composition as well.

DESCRIPTION OF EMBODIMENTS

A peptide composition of the present invention includes: a peptide; a buffering agent having a pKa of 3.5 or more and less than 7.5 and containing one or more nitrogen atoms; and water, and has a pH of from 4.5 to 6.6. Through the use of such buffering agent, there is provided a peptide composition that can achieve both excellent storage stability and desired characteristics (e.g., transparency).

The peptide composition has a pH of from 4.5 to 6.6, preferably from 4.6 to 6.5, more preferably from 5.0 to 6.0. When the pH of the peptide composition falls within the above-mentioned range, the storage stability of the peptide composition can be further improved. In addition, even when the peptide to be used contains an amide group in its structure, the degradation of the amide group is suppressed, and hence excellent storage stability can be achieved. In addition, the effect of the present invention can be particularly exhibited when a peptide in which the amino acid at its C-terminus is a basic amino acid and its C-terminus is an amide group is used. This is because, when the pH falls outside the above-mentioned range, there is a risk that a degradation reaction of the C-terminal amide group may occur, involving the nitrogen atom of the side chain of the basic amino acid, to generate a peptide having a C-terminal carboxylic acid.

The peptide composition has a visible light transmittance of preferably 70% or more, more preferably 85% or more, still more preferably 90% or more, particularly preferably 95% or more. When the visible light transmittance of the peptide composition falls within the above-mentioned range, the peptide composition can be suitably used even in an application requiring transparency. Herein, the visible light transmittance is a light transmittance at wavelengths of from 380 nm to 780 nm and may be measured using, for example, a spectrophotometer (specifically a product manufactured under the product name of Nano Drop 2000 by Thermo Fisher Scientific).

A. Self-Assembling Peptide

The peptide to be contained in the peptide composition of the present invention is a self-assembling peptide. The self-assembling peptide is expected to find use in various fields, such as regenerative medicine and cell culture, by virtue of its characteristics. In the peptide composition of the present invention, the self-assembling peptide can satisfactorily maintain its self-assembling property. Accordingly, a suitable function can be retained not only during a storage period, but also after application to a desired application.

Herein, the "self-assembling peptide" refers to a peptide that spontaneously assembles in a solvent through an interaction between peptide molecules. The interaction is not particularly limited, and examples thereof include: electrostatic interactions, such as hydrogen bonding, an interionic interaction, and a van der Waals force; and a hydrophobic interaction. Of the self-assembling peptides, a peptide that self-assembles through a β-sheet structure is particularly preferred. The β-sheet structure typically has a surface having relatively high hydrophilicity and a surface having relatively low hydrophilicity. In general, when a composition is prepared by dissolving a self-assembling peptide in a solvent, such as water, the composition often turns into a gel through the above-mentioned interaction between peptide molecules. The formation of the β-sheet structure may be confirmed by, for example, measuring the molar ellipticity of the peptide composition by a circular dichroism measurement method, and confirming the molar ellipticity at 216 nm to have a negative value. In addition, the formation of the β-sheet structure may also be confirmed by detecting a peak attributed to a β-sheet appearing around 1,620 cm$^{-1}$ or a peak attributed to an antiparallel β-sheet appearing around 1,690 cm$^{-1}$ through the use of FT-IR analysis.

In the present invention, the self-assembling peptide and the buffering agent are used together. Therefore, the peptide preferably has an ion to be paired with the buffering agent to be used. As described later, it is suitable to use, as the buffering agent, a buffering agent showing a buffering action on the basis of a change between a state in which the electron pair of a nitrogen atom serving a buffering action does not have added thereto a proton in a buffering agent molecule (in this case, the formal charge of the nitrogen atom is ±0) and a state in which the electron pair of the nitrogen atom has added thereto a proton (in this case, the formal charge of the nitrogen atom is a positive charge). Therefore, the form of a peptide having an ion (anion) to be paired with the buffering agent in a state in which the electron pair of the nitrogen has added thereto a proton, for example, the form of a salt, such as a hydrochloride of a peptide, a trifluoroacetate of a peptide, or a methanesulfonate of a peptide (preferably a salt with an acid (e.g., a strong acid having a pKa of <3)), is preferred. The peptide having an ion to be paired with the buffering agent in a state in which the electron pair of the nitrogen has added thereto a proton may be used in combination with a peptide having no ion to be paired with the buffering agent.

In addition, it is generally considered that, when a self-assembling peptide is combined with a salt, the charge of the peptide is shielded with a charge (ion) generated from the salt to direct peptide molecules into assembling with each other. Accordingly, the salt is sometimes added to facilitate the assembly of the peptide. Meanwhile, however, peptide molecules excessively approach each other in a random manner owing to the salt, often resulting in aggregation of the peptide. The aggregation of the peptide may cause the lowering of transparency due to white turbidity and the lowering of mechanical stability as a gel composition (specifically embrittlement or syneresis). In contrast, in the present invention, a self-assembling peptide having a positive total charge of amino acid residues contained in the peptide at the pH of the peptide composition is particularly suitably used. In the case where the peptide having a positive total charge is used, when the peptide is combined with a buffering agent containing one or more nitrogen atoms, an appropriate electrostatic repulsion is maintained between peptide molecules in the composition, and hence the peptide is less liable to aggregate. The buffering agent also generates a charge in water, but the composition of the present invention has a desired buffering action and transparency, and also has high stability against mechanical treatment and hence can maintain mechanical stability as a gel composition even after being subjected to treatment, such as agitation and mixing, a plurality of times.

The total charge of the amino acid residues contained in the self-assembling peptide is preferably more than 0 and +3 or less, more preferably from +1 to +3, in the composition containing the peptide (i.e., the peptide composition of the present invention). This is because, when a positive charge and a negative charge that are derived from the side chains of the amino acid residues are not offset with each other in the composition as described above, a balance between an electrostatic attraction and repulsion suited for the formation of a gel is maintained, and as a result, a transparent and stable gel can be formed.

The charge of the self-assembling peptide may be calculated with a program available on the website of PROTEIN CALCULATOR v3.4 (http://protcalc.sourceforge.net/).

The self-assembling peptide to be used in the present invention preferably has an amide group at its C-terminus (having its C-terminal carboxyl group amidated). The amide group is a functional group in which electrons are delocalized, and hence is a stable functional group that is relatively less liable to degrade. Therefore, the amide group may be used as a protecting group. However, its degradation may occur under each of an acidic condition and a basic condition, and the degradation may occur even at a near neutral pH. In the present invention, the buffering agent having a pKa of from 3.5 to 7.5 and containing one or more nitrogen atoms, which is described in the section B below, is used and the composition is adjusted to a pH of from 4.5 to 6.6. Accordingly, a peptide composition excellent in storage stability can be obtained even with the peptide having an amide group at its C-terminus.

In one embodiment, the amino acid at the C-terminus of the self-assembling peptide is preferably a basic amino acid, such as arginine, lysine, or histidine, more preferably arginine or lysine, still more preferably arginine. When a peptide in which the amino acid at its C-terminus is a basic amino acid and its C-terminus is an amide group is used, a degradation reaction of the C-terminal amide group may occur, involving the nitrogen atom of the side chain of the basic amino acid, to generate a peptide having a C-terminal carboxylic acid. Accordingly, such peptide may have a problem particularly with storage stability. However, according to the present invention, an effect of achieving both storage stability and desired effects can be suitably achieved.

As the self-assembling peptide, for example, a self-assembling peptide described in JP 2010-280719A may be suitably used. The entire description of the laid-open publication is incorporated herein by reference. This self-assembling peptide is formed of an amino acid sequence of 13 residues having basic amino acid residues (at positions 1, 5, 9, and 13) and acidic amino acid residues (at positions 3 and 11) every other residue at symmetric positions in the N-terminal direction and the C-terminal direction with respect to a hydrophobic amino acid residue at position 7 in the center. That is, one feature of this self-assembling peptide resides in that the self-assembling peptide does not have hydrophilic amino acids and hydrophobic amino acids alternately. In addition, another feature of this self-assembling peptide resides in that the self-assembling peptide does not have hydrophilic amino acid residues and hydrophobic amino acid residues at equal ratios. In addition, still another feature of this self-assembling peptide resides in that the self-assembling peptide has four basic amino acid residues and two acidic amino acid residues at predetermined symmetric positions with respect to a hydrophobic amino acid residue at position 7 in the center, and both of amino acid residues at the N-terminus and the C-terminus are basic amino acid residues.

Specifically, a self-assembling peptide formed of the following amino acid sequence is given.
Amino acid sequence: $a_1 b_1 c_1 b_2 a_2 b_3 d b_4 a_3 b_5 c_2 b_6 a_4$ (In the amino acid sequence, $a_1$ to $a_4$ each represent a basic amino acid residue, $b_1$ to $b_6$ each represent an uncharged polar amino acid residue and/or a hydrophobic amino acid residue, provided that at least five thereof each represent a hydrophobic amino acid residue, $c_1$ and $c_2$ each represent an acidic amino acid residue, and d represents a hydrophobic amino acid residue).

The self-assembling peptide represented by the amino acid sequence is capable of forming a gel excellent in transparency and mechanical strength, and hence can be suitably used in various applications. Meanwhile, this self-assembling peptide has basic amino acid residues at its termini as described above, and hence has room for improvement in storage stability. When this self-assembling peptide is used as the peptide to be contained in the peptide composition of the present invention, a peptide composition retaining the above-mentioned excellent characteristics and also being excellent in storage stability can be provided.

The self-assembling peptide that may be suitably used in the present invention is not limited to the one given above as an example. Specific examples of the self-assembling peptide that may be suitably used in the present invention include the following, including the one given above as an example.

```
                                        (SEQ ID NO: 1)
        n-RLDLRLALRLDLR-c (SEQ ID NO: 2)
        n-RLDLRLSLRLDLR-c (SEQ ID NO: 3)
        n-RLALRLDLRLDLR-c (SEQ ID NO: 4)
        n-KRLDLNLRLDLRK-c
```

The self-assembling peptide may be produced by any appropriate production method. Examples thereof include: a chemical synthesis method, such as a solid-phase method, for example, an Fmoc method, or a liquid-phase method; and a molecular biological method, such as gene recombinant expression. Those production methods (in particular, a chemical synthesis method) may include a purification step and/or deprotection step involving using an acid. In such production method, because it is difficult to completely remove the acid from the peptide, the peptide to be obtained may have mixed therein a very slight amount of the acid, and hence may show a lower pH (e.g., pH≤4.0) than a theoretical value when dissolved in water. A peptide composition using such peptide can be provided with a buffering action simultaneously with being adjusted to a desired pH with the buffering agent to be described later.

Amino acids constituting the self-assembling peptide may each be an L-amino acid or a D-amino acid. In addition, the amino acids may each be a natural amino acid or a non-natural amino acid. A natural amino acid is preferred because the natural amino acid is available at low price and facilitates peptide synthesis.

The self-assembling peptide to be used in the present invention may be a peptide that has been subjected to any appropriate modification (hereinafter referred to as modified peptide). In the modified peptide, the peptide may be subjected to any appropriate modification as long as the peptide has desired characteristics (e.g., a self-assembling ability) and does not affect the storage stability of the peptide composition. A site at which the modification is performed may be the N-terminal amino group of the peptide, its C-terminal carboxyl group, or both thereof.

Examples of the modification include: introduction of a protecting group, such as acetylation of the N-terminus or amidation of the C-terminus; introduction of a functional group, such as alkylation, esterification, or halogenation; hydrogenation; introduction of a saccharide compound, such as a monosaccharide, a disaccharide, an oligosaccharide, or a polysaccharide; introduction of a lipid compound, such as a fatty acid, a phospholipid, or a glycolipid; introduction of DNA; and introduction of, for example, any other compound having physiological activity. The modifications may be performed alone or in combination thereof. For example, the peptide may have its N-terminus acetylated and its C-terminus amidated. As described above, the effect of the present invention can be suitably obtained in a peptide composition containing a self-assembling peptide having an amide group at its C-terminus, and hence a modified peptide having an amide group introduced as a protecting group at its C-terminus may be suitably used.

The modification may be performed by any appropriate method depending on, for example, the kind of the modification.

The number of amino acid residues constituting the self-assembling peptide is not particularly limited. From the viewpoint of suitably exhibiting a self-assembling ability, the number of the amino acid residues is preferably from 2 to 200, more preferably from 2 to 20, still more preferably from 6 to 20, particularly preferably from 12 to 20, most preferably from 13 to 15.

The content of the self-assembling peptide in the peptide composition is set to any appropriate value depending on, for example, purposes. The peptide composition of the present invention contains the self-assembling peptide at a concentration of, for example, from 0.01 w/w % to 10 w/w %, preferably from 0.1 w/w % to 3.0 w/w %, more preferably from 0.5 w/w % to 3.0 w/w %, still more preferably from 0.5 w/w % to 2.5 w/w %, most preferably from 1.0 w/w % to 2.0 w/w %.

B. Buffering Agent

In the present invention, a buffering agent having a pKa of 3.5 or more and less than 7.5 and containing one or more nitrogen atoms is used. Through the use of such buffering agent, both the storage stability and desired characteristics (e.g., transparency) of the peptide composition can be achieved. In particular, when a peptide having an amide group at its C-terminus is used as the self-assembling peptide, the effect of the present invention can be further exhibited. The amide group may be used as a protecting group for the C-terminus of the peptide. The amide group is known to degrade under each of an acidic condition and a basic condition. In addition, even under a neutral condition, it is difficult to completely suppress the degradation of the amide group. Accordingly, the amide group serving as the protecting group is removed and degraded into a carboxyl group during storage, and desired characteristics of the peptide are impaired in some cases. Further, there is also a risk that a by-product produced by the degradation may serve as an impurity to lower the quality of the peptide composition. In the peptide composition of the present invention, through the use of the buffering agent having a pKa of 3.5 or more and less than 7.5 and containing one or more nitrogen atoms, the peptide composition can be maintained for a long period of time at a pH at which the degradation of the peptide can be suppressed. Accordingly, a peptide composition that can achieve both storage stability and desired characteristics can be obtained. Further, when a buffering agent is used in a peptide composition, there is also a problem in that its preparation at a constant pH is difficult owing to the vaporization of the buffering agent or the like, resulting in a batch-to-batch variation. In the case of the buffering agent to be used in the present invention, its content in the peptide composition is less liable to be decreased by vaporization or the like. Accordingly, the peptide composition can maintain a temporally stable pH. The use of the above-mentioned buffering agent facilitates the control of the pH of the peptide composition, and hence can suppress the batch-to-batch variation in quality as well.

The pKa of the buffering agent is 3.5 or more and less than 7.5, preferably from 3.8 to 7.2, more preferably from 4.5 to 6.5. When the pKa of the buffering agent falls within the above-mentioned range, both the storage stability and desired characteristics of the peptide composition to be obtained can be achieved. In addition, the use of such buffering agent facilitates the control of the pH of the peptide composition, and hence can prevent the batch-to-batch variation in quality as well. A buffering agent that undergoes multistage dissociation has a plurality of pKa's. In the case of using such buffering agent, a buffering agent in which at least one of the plurality of pKa's falls within the above-mentioned range is used. A pKa value may be measured at room temperature (about 23° C.) using any appropriate measurement apparatus, or a value described in the literature may be referred to and used. Herein, reference is made to values described in the following literatures: Chemical Handbook Fundamentals II revised 3rd edition, edited by The Chemical Society of Japan, 1984 (ethylenediamine and histidine); Kiyoshi Sawada and Daijiro Ohmori, Buffers: Principle and Practice, 2009 (bis-Tris); edited by the Society of Japanese Pharmacopoeia, Collection of Information on the Quality of Prescription Drugs No. 23, 2005 (thiamine nitrate); Brown, H. C. et al., in Braude, E. A. and F. C. Nachod, Determination of Organic Structures by Physical Methods, 1955 (pyridine); and Hall, H. K., Jr. J. A.m. Soc. 1957, 79, 5441 (N-methylmorpholine).

The buffering agent contains one or more nitrogen atoms. The buffering agent is a basic buffering agent, and is typically capable of showing a buffering action on the basis of a weak base and its conjugate acid. In other words, the buffering agent is capable of showing a buffering action on the basis of a change between a state in which the electron pair of a nitrogen atom does not have added thereto a proton (the formal charge of the nitrogen atom is ±0) and a state in which the electron pair of the nitrogen atom has added thereto a proton (the formal charge of the nitrogen atom is a positive charge). In addition, when the buffering agent is combined with a salt thereof, a more suitable buffering action can be obtained. Herein, with regard to such buffering agent, the pKa of the state in which the electron pair of the nitrogen atom has added thereto a proton, that is, the pKa of the conjugate acid is regarded as the pKa of the buffering agent. The use of such buffering agent prevents aggregation of the peptide, and hence a peptide composition having higher transparency can be obtained. Further, from a different viewpoint, the buffering agent is preferably monomolecular. In addition, from a different viewpoint, the buffering agent is preferably a substance containing no sulfonic acid group.

In one embodiment, the buffering agent is a compound having one or more basic functional groups whose conjugate acids each have a pKa of 3.5 or more and less than 7.5, preferably from 3.8 to 7.2, more preferably from 4.5 to 6.5. An example of the basic functional group is an amino group or a nitrogen-containing heterocycle. The amino group may be any of a primary amino group (—NH$_2$), a secondary amino group (—NHR), and a tertiary amino group (—NRR'). In addition, the number of the basic functional groups in the compound may be, for example, 4 or less, preferably 3 or less. The compound may further have an acidic or basic functional group having a pKa of less than 3.5 or 7.5 or more as long as the effect of the present invention is not impaired. In addition, the molecular weight of the compound may be, for example, from 50 to 400, preferably from 60 to 350.

Specific examples of the buffering agent suitable in the present invention include ethylenediamine (pKa: 7.1 (25° C.)), histidine (pKa: 6.0 (25° C.)), bis-Tris (pKa: 6.5 (20° C.)), thiamine nitrate (pKa: 4.8), pyridine (pKa: 5.2 (20° C.)), 1-methylimidazole (pKa: 7.1), and N-methylmorpholine (pKa: 7.4) (only a pKa of 3.5 or more and less than 7.5 is described). Of those, histidine and/or bis-Tris are preferred. With any of those buffering agents, a highly biocompatible peptide composition can be easily obtained. The buffering agents may be used alone or in combination thereof.

The concentration of the buffering agent in the peptide composition only needs to be such a concentration that the peptide composition has a desired pH. From the viewpoint of suitably exhibiting a buffering action, the concentration of the buffering agent is preferably from 1 mM to 100 mM, more preferably from 5 mM to 50 mM, still more preferably from 15 mM to 50 mM, still even more preferably from 20 mM to 50 mM, most preferably from 30 mM to 50 mM.

C. Water

Any appropriate water may be used as the water to be contained in the peptide composition. Examples thereof include distilled water (e.g., water for injection) and deionized water.

D. Additive

The peptide composition of the present invention may contain any appropriate additive in addition to the self-assembling peptide, the buffering agent having a pKa of 3.5 or more and less than 7.5 and containing one or more nitrogen atoms, and the water, depending on, for example, applications. Examples thereof include: a tonicity agent; and saccharides, such as a monosaccharide, a disaccharide, and an oligosaccharide. The additives may be added alone or in combination thereof. The concentration of the additive may be appropriately set depending on, for example, purposes, and applications of the peptide composition.

Examples of the tonicity agent include: chlorides, such as sodium chloride, potassium chloride, calcium chloride, and magnesium chloride; monosaccharides, such as glucose, fructose, and galactose; disaccharides, such as sucrose, trehalose, maltose, and lactose; and sugar alcohols, such as mannitol and sorbitol.

In addition, the peptide composition of the present invention may further contain a component having an ion to be paired with the buffering agent in a state in which the electron pair of a nitrogen atom contained in the buffering agent has added thereto a proton. An example of such component is a salt of an acid, such as hydrochloric acid, trifluoroacetic acid, or methanesulfonic acid (e.g., a strong acid having a pKa of <3), and an inorganic compound or an organic compound (e.g., a sodium salt, or a peptide salt other than the self-assembling peptide).

E. Production Method for Peptide Composition

The peptide composition of the present invention may be produced by any appropriate production method. The production method preferably includes agitating a self-assembling peptide, a buffering agent having a pKa of 3.5 or more and less than 7.5 and containing one or more nitrogen atoms, and water. For example, the self-assembling peptide is dissolved in water so as to have a desired concentration to prepare a peptide aqueous solution, any appropriate additive is further added as required, and then the buffering agent is added so that the mixture has a pH of from 4.5 to 6.6. Then, those components are agitated as required using any appropriate agitating means. Thus, the peptide composition may be obtained. In one embodiment, the peptide composition immediately after the preparation may show a form having fluidity (e.g., a liquid or sol form) depending on, for example, the peptide concentration. A peptide composition in a form that has lost fluidity (e.g., a gel form) may be obtained by, for example, leaving the peptide composition in the form having fluidity at rest to allow the self-assembling peptide to self-assemble.

As the agitating means, for example, a propeller, a rod, a magnetic stirrer, a rotation-revolution agitator (as well as its combined use with a container having unevenness on its inside), an ultrasonic homogenizer, or a sonicator may be used. Herein, the agitation encompasses operations each of which means a state other than a rest state, such as stirring, stirring around, mixing, bubbling, and vibration.

In addition, the buffering agent may be separately dissolved in water to prepare a buffer solution, and the peptide composition may be prepared using the buffer solution. Further, the peptide, the buffering agent, and any appropriate additive may be charged into water, and then agitated. The charging may be gradually performed, may be performed for each component, or may be performed at once. In addition, water may be charged into the peptide, the buffering agent, and any appropriate additive, and then these components may be agitated.

In addition, the peptide composition may be subjected to heating treatment as required. In the present invention, the nitrogen atom-containing buffering agent is used, and hence volatilization and degradation of the buffering agent due to heating can be suppressed. Accordingly, while a sterilization or bactericidal effect of the heating is obtained, the composition can be maintained at a desired pH even after the heating, and hence there is an advantage particularly for long-term storage of the composition. The treatment temperature of the heating treatment is, for example, 100° C. or more, preferably from 120° C. to 130° C. In addition, the treatment time is, for example, 10 seconds or more, preferably from 1 minute to 30 minutes, more preferably from 15 minutes to 25 minutes. The heating treatment may be performed under increased pressure. A specific example of the heating treatment is autoclave treatment (e.g., treatment at 121° C. and 2 atm for from 15 minutes to 25 minutes).

F. Applications of Peptide Composition

The peptide composition of the present invention can achieve both storage stability and desired characteristics. Accordingly, the peptide composition of the present invention can be applied to various applications utilizing the characteristics of the peptide composition. When the peptide composition of the present invention contains an artificially synthesized peptide, the peptide composition is free of the risk of an infection of animal origin, and hence can be preferably used in applications targeted to humans. Specific examples of the applications targeted to humans include: cosmetics, such as a skin care article and a hair care article; a cell culture substrate to be used for drug development screening, regenerative medicine, or the like, and drugs and medical instruments, such as a pressure ulcer preparation, a bone filling injection material, an injection material for cosmetic surgery, an auxiliary material for ophthalmic surgery, a synthetic vitreous, an intraocular lens, a joint lubricant, an eye drop, a drug delivery system (DDS) substrate, a carrier for cell delivery, a hemostatic material, and an occlusive agent; a lubricating humectant; a desiccant; a coating agent for a medical instrument or the like; and a material for preventing the outflow of a liquid, a gas, or the like.

When a related-art peptide composition is agitated in a state of containing a buffering agent, its transparency is impaired by aggregation and turbidity in some cases, and a peptide composition in a desired form (e.g., a gel) cannot be prepared in some cases. However, the peptide composition of the present invention, in which such problems have been solved, can be suitably used even in an application requiring transparency or the like.

The peptide composition of the present invention has a pH of from 4.5 to 6.6. The peptide composition may be used by being adjusted at the time of use to a desired pH outside the above-mentioned range depending on its applications.

In addition, the fluidity of the peptide composition of the present invention can be temporarily increased by applying a physical force or stimulation thereto. Further, the peptide composition of the present invention can have a feature in that the fluidity lowers again after a while and its strength before the application of the physical force or stimulation is regained. For example, a composition using the self-assembling peptide described in JP 2010-280719 A can have such physical properties. Therefore, the peptide composition of the present invention can be suitably used in applications requiring such characteristics (e.g., an application in which the peptide composition is applied through ejection with a syringe or the like).

Now, the present invention is specifically described by way of Examples. However, the present invention is not limited by these Examples.

Example 1

A hydrochloride of a self-assembling peptide A set forth in SEQ ID NO: 1 synthesized by a liquid-phase synthesis method and having its N-terminus acetylated and its C-terminus amidated ([CH₃CO]-RLDLRLALRLDLR-[NH₂]) was used.

The peptide A hydrochloride and water for injection (manufactured by Fuso Pharmaceutical Industries, Ltd., product name: Water for Injection PL "Fuso") were placed in a vial and agitated to obtain a peptide aqueous solution. To the obtained peptide aqueous solution, histidine (manufactured by Wako Pure Chemical Industries, Ltd., product name: L-Histidine, pKa: 6.0) was added as a buffering agent. Then, water for injection was added to a peptide concentration of 0.5 w/w % and a histidine concentration of 7 mM, and the contents were further agitated to obtain a peptide composition 1. The obtained composition had a pH of 5.52. The composition of the obtained peptide composition is shown in Table 1.

TABLE 1

| | Peptide composition | | | | |
|---|---|---|---|---|---|
| | Peptide | | | Buffering agent | |
| | No. | Kind | Concentration [w/w %] | Kind | pKa |
| Example 1 | 1 | A | 0.5 | Histidine | 6.0 |
| Comparative Example 1 | C1 | | 0.5 | Sodium carbonate | 6.4 |

TABLE 1-continued

| | Peptide composition | | | | |
|---|---|---|---|---|---|
| | Peptide | | | Buffering agent | |
| | No. | Kind | Concentration [w/w %] | Kind | pKa |
| Example 2 | 2 | | 1.5 | Histidine | 6.0 |
| Comparative Example 2 | C2 | | 1.5 | Sodium carbonate | 6.4 |
| Example 3 | 3 | | 2.5 | Histidine | 6.0 |
| Comparative Example 3 | C3 | | 2.5 | Sodium carbonate | 6.4 |
| Example 4 | 4 | | 1.5 | Histidine | 6.0 |
| Example 5 | 5 | | 1.5 | Thiamine nitrate | 4.8 |
| Example 6 | 6 | | 1.5 | Pyridine | 5.2 |
| Example 7 | 7 | | 1.5 | Bis-Tris | 6.5 |
| Example 8 | 8 | | 1.5 | Ethylenediamine | 7.1 |
| Example 9 | 9 | | 1.5 | N-Methylmorpholine | 7.4 |
| Comparative Example 4 | C4 | | 1.5 | Trometamol (Tris) | 8.3 |
| Example 10 | 10 | B | 1.5 | Histidine | 6.0 |
| Comparative Example 5 | C5 | | | Sodium carbonate | 6.4 |
| Example 11 | 11 | C | 1.5 | Histidine | 6.0 |
| Comparative Example 6 | C6 | | | Sodium carbonate | 6.4 |
| Example 12 | 12 | D | 1.5 | Histidine | 6.0 |
| Comparative Example 7 | C7 | | | Sodium carbonate | 6.4 |
| Example 13 | 13 | E | 0.5 | Histidine | 6.0 |
| Example 14 | 14 | | | Thiamine nitrate | 4.8 |
| Comparative Example 8 | C8 | | | Sodium carbonate | 6.4 |
| Comparative Example 9 | C9 | A | 1.5 | Sodium citrate | 6.4 |
| Comparative Example 10 | C10 | | | Maleic acid | 5.8 |

Peptide A: peptide set forth in SEQ ID NO: 1 (amino acid sequence: Ac-RLDLRLAL-RLDLR-NH₂) obtained by liquid-phase synthesis
Peptide B: peptide set forth in SEQ ID NO: 1 (amino acid sequence: Ac-RLDLRLAL-RLDLR-NH₂) obtained by solid-phase synthesis
Peptide C: peptide set forth in SEQ ID NO: 2 (amino acid sequence: Ac-RLDLRLSL-RLDLR-NH₂) obtained by solid-phase synthesis
Peptide D: peptide set forth in SEQ ID NO: 3 (amino acid sequence: Ac-RLALRLDL-RLDLR-NH₂) obtained by solid-phase synthesis
Peptide E: peptide set forth in SEQ ID NO: 4 (amino acid sequence: Ac-KRLDLNL-RLDLRK-NH₂) obtained by solid-phase synthesis Comparative Example 1

A peptide composition C1 was obtained in the same manner as in Example 1 except that: sodium carbonate (manufactured by Wako Pure Chemical Industries, Ltd., product name: Sodium Carbonate, pKa: 6.4) was used as the buffering agent; and the composition was prepared so that the concentration of the buffering agent in the composition to be obtained was 5 mM. The obtained composition had a pH of 7.42. The composition of the obtained peptide composition is shown in Table 1.

Example 2

A peptide composition 2 was obtained in the same manner as in Example 1 except that the composition was prepared so as to have a peptide concentration of 1.5 w/w % and a histidine concentration of 31 mM. The obtained composition had a pH of 6.14. The composition of the obtained peptide composition is shown in Table 1.

Comparative Example 2

A peptide composition C2 was obtained in the same manner as in Comparative Example 1 except that the composition was prepared so as to have a peptide concentration of 1.5 w/w % and a sodium carbonate concentration of 13 mM. The obtained composition had a pH of 7.12. The composition of the obtained peptide composition is shown in Table 1.

Example 3

A peptide composition 3 was obtained in the same manner as in Example 1 except that the peptide aqueous solution was prepared so as to have a peptide concentration of 2.5 w/w % and a histidine concentration of 38 mM. The obtained composition had a pH of 5.91. The composition of the obtained peptide composition is shown in Table 1.

Comparative Example 3

A peptide composition C3 was obtained in the same manner as in Comparative Example 1 except that the composition was prepared so as to have a peptide concentration of 2.5 w/w % and a sodium carbonate concentration of 23 mM. The obtained composition had a pH of 7.65. The composition of the obtained peptide composition is shown in Table 1.

Example 4

A peptide composition 4 was obtained in the same manner as in Example 2 except that the composition was prepared by adding trehalose dihydrate so that its concentration in the composition to be obtained was 7 w/w %. The obtained composition had a pH of 6.06. The composition of the obtained peptide composition is shown in Table 1.

Example 5

A peptide composition 5 was obtained in the same manner as in Example 2 except that: thiamine nitrate (manufactured by Kanto Chemical Co., Inc., product name: Thiamine Nitrate, pKa: 4.8) was used as the buffering agent; and the composition was prepared so as to have a thiamine nitrate concentration of 38 mM. The obtained composition had a pH of 5.08. The composition of the obtained peptide composition is shown in Table 1.

Example 6

A peptide composition 6 was obtained in the same manner as in Example 2 except that: pyridine (manufactured by Nacalai Tesque Inc., product name: Pyridine, pKa: 5.2) was used as the buffering agent; and the composition was prepared so as to have a pyridine concentration of 22 mM. The obtained composition had a pH of 4.70. The composition of the obtained peptide composition is shown in Table 1.

Example 7

A peptide composition 7 was obtained in the same manner as in Example 2 except that bis-Tris (manufactured by Dojindo Laboratories, product name: Bis-Tris, pKa: 6.5) was used as the buffering agent. The obtained composition had a pH of 6.51. The composition of the obtained peptide composition is shown in Table 1.

Example 8

A peptide composition 8 was obtained in the same manner as in Example 2 except that: ethylenediamine (manufactured by Kanto Chemical Co., Inc., product name: Ethylenediamine (Anhydrous), pKa: 7.1) was used as the buffering agent; and the composition was prepared so as to have an ethylenediamine concentration of 9 mM. The obtained composition had a pH of 5.85. The composition of the obtained peptide composition is shown in Table 1.

Example 9

A peptide composition 9 was obtained in the same manner as in Example 2 except that: N-methylmorpholine (manufactured by Kanto Chemical Co., Inc., product name: N-Methylmorpholine, pKa: 7.4) was used as the buffering agent; and the composition was prepared so as to have an N-methylmorpholine concentration of 17 mM. The obtained composition had a pH of 6.10. The composition of the obtained peptide composition is shown in Table 1.

Comparative Example 4

A peptide composition C4 was obtained in the same manner as in Example 2 except that: trometamol (trishydroxymethylaminomethane) (manufactured by Wako Pure Chemical Industries, Ltd., product name: Trometamol "For Production Use Only", pKa: 8.3) was used as the buffering agent; and the composition was prepared so as to have a trometamol concentration of 30 mM. The obtained composition had a pH of 8.13. The composition of the obtained peptide composition is shown in Table 1.

Example 10

A hydrochloride of the self-assembling peptide B having the amino acid sequence set forth in SEQ ID NO: 1 synthesized by a solid-phase synthesis method and having its N-terminus acetylated and its C-terminus amidated ([CH$_3$CO]-RLDLRLALRLDLR-[NH$_2$]) was used.

A peptide composition 10 was obtained in the same manner as in Example 2 except that: the hydrochloride of the peptide B was used; and the composition was prepared so as to have a histidine concentration of 22 mM. The obtained composition had a pH of 5.51. The composition of the obtained peptide composition is shown in Table 1.

Comparative Example 5

A peptide composition C5 was obtained in the same manner as in Comparative Example 2 except that: the hydrochloride of the peptide B was used; and the composition was prepared so as to have a sodium carbonate concentration of 14 mM. The obtained composition had a pH of 6.94. The composition of the obtained peptide composition is shown in Table 1.

Example 11

A hydrochloride of the self-assembling peptide C having the amino acid sequence set forth in SEQ ID NO: 2 synthesized by a solid-phase synthesis method and having its N-terminus acetylated and its C-terminus amidated ([CH$_3$CO]-RLDLRLSLRLDLR-[NH$_2$]) was used.

A peptide composition 11 was obtained in the same manner as in Example 2 except that: the hydrochloride of the peptide C was used; and the composition was prepared so as to have a histidine concentration of 22 mM. The obtained composition had a pH of 5.54. The composition of the obtained peptide composition is shown in Table 1.

Comparative Example 6

A peptide composition C6 was obtained in the same manner as in Comparative Example 2 except that: the hydrochloride of the peptide C was used; and the composition was prepared so as to have a sodium carbonate concentration of 12 mM. The obtained composition had a pH of 7.12. The composition of the obtained peptide composition is shown in Table 1.

Example 12

A hydrochloride of the self-assembling peptide D having the amino acid sequence set forth in SEQ ID NO: 3 synthesized by a solid-phase synthesis method and having its N-terminus acetylated and its C-terminus amidated ([CH$_3$CO]-RLALRLDLRLDLR-[NH$_2$]) was used.

A peptide composition 12 was obtained in the same manner as in Example 2 except that: the hydrochloride of the peptide D was used; and the composition was prepared so as to have a histidine concentration of 22 mM. The obtained composition had a pH of 5.73. The composition of the obtained peptide composition is shown in Table 1.

Comparative Example 7

A peptide composition C7 was obtained in the same manner as in Comparative Example 2 except that: the hydrochloride of the peptide D was used; and the composition was prepared so as to have a sodium carbonate concentration of 12 mM. The obtained composition had a pH of 7.22. The composition of the obtained peptide composition is shown in Table 1.

Example 13

A trifluoroacetate of the self-assembling peptide E having the amino acid sequence set forth in SEQ ID NO: 4 synthesized by a solid-phase synthesis method and having its N-terminus acetylated and its C-terminus amidated ([CH$_3$CO]-KRLDLNLRLDLRK-[NH$_2$]) was used.

A peptide composition 13 was obtained in the same manner as in Example 1 except that: the trifluoroacetate of the peptide E was used; and the composition was prepared so as to have a histidine concentration of 43 mM. The obtained composition had a pH of 5.51. The composition of the obtained peptide composition is shown in Table 1.

Example 14

A peptide composition 14 was obtained in the same manner as in Example 13 except that: thiamine nitrate (manufactured by Kanto Chemical Co., Inc., product name: Thiamine Nitrate, pKa: 4.8) was used as the buffering agent; and the composition was prepared so as to have a thiamine nitrate concentration of 5 mM. The obtained composition had a pH of 4.56. The composition of the obtained peptide composition is shown in Table 1.

Comparative Example 8

A peptide composition C8 was obtained in the same manner as in Comparative Example 1 except that: the trifluoroacetate of the peptide E was used; and the composition was prepared so as to have a sodium carbonate concentration of 3 mM. The obtained composition had a pH of 7.42. The composition of the obtained peptide composition is shown in Table 1.

Comparative Example 9

A peptide composition C9 was obtained in the same manner as in Comparative Example 2 except that: sodium citrate (manufactured by Wako Pure Chemical Industries, Ltd., product name: Sodium Citrate, pK$_1$: 3.1, pK$_2$: 4.8, pK$_3$: 6.4) was used as the buffering agent; and the composition was prepared so that the concentration of the buffering agent in the composition to be obtained was 20 mM and the concentration of trehalose dihydrate therein was 8 w/w %. The composition of the obtained composition is shown in Table 1.

Comparative Example 10

A peptide composition C10 was obtained in the same manner as in Comparative Example 2 except that: maleic acid (manufactured by Tokyo Chemical Industry Co., Ltd., product name: Maleic Acid, pK$_2$: 1.84, pK$_2$: 5.83) was used as the buffering agent; the composition was prepared so that the concentration of the buffering agent in the composition to be obtained was 19 mM; trometamol (trishydroxymethylaminomethane) (manufactured by Wako Pure Chemical Industries, Ltd., product name: Trometamol "For Production Use Only", pKa: 8.3) was used as a neutralizer; and the composition was prepared so as to have a trometamol concentration of 50 mM. The composition of the obtained composition is shown in Table 1.

The following storage and measurement were performed using the obtained peptide compositions 1 to 14 and C1 to C10. Storage conditions are shown in Table 2, and measurement results are shown in Table 3 and Table 4.

[Storage of Peptide Composition]

Each composition was stored by the following operation.

A half of the obtained peptide composition in the vial was dispensed into a fresh vial of the same kind, and each of the two vials was sealed.

A composition subjected to autoclave treatment (AC treatment) was subjected to sterilization treatment under the conditions of 121° C. and 20 minutes.

One of the two vials was stored under conditions shown in Table 2. When stored at 40° C. (humidity: 75%), the vial was stored in a thermo-hygrostat chamber LH21-13M (manufactured by Nagano Science Co., Ltd.), and when stored at 60° C. (humidity: 75%), the vial was stored in a thermo-hygrostat CSH-210 (manufactured by Tabai Espec Corporation).

The number of days 6 times the number of days of storage and the number of days 50 times the number of days of storage were defined as a substantial storage period (room temperature storage-equivalent period) for the vial stored at 40° C. and the vial stored at 60° C., respectively.

The other vial was opened as a sample before storage, and subjected to HPLC measurement and light transmittance measurement. In addition, the vial was sealed unless needed, and was stored at room temperature after measurement.

[pH Measurement]

Measurement was performed using a pH meter (manufactured by Horiba, Ltd., product name: B-712 (main body), S010 (sensor)).

[Increase Amount of Content of Degradation Product]

The peptide used for the preparation of each composition (hereinafter referred to as "raw material"), and the peptide composition after storage were analyzed by reversed-phase chromatography by HPLC. In addition, the peptide composition after autoclave treatment (before storage) was also analyzed.

Measurement conditions are shown below. As apparent from the following measurement conditions, the measurement conditions are measurement conditions utilizing optical absorption of a peptide bond, and a peptide component of the composition is detected as a peak under the conditions.

HPLC: manufactured by Waters, 717Auto sampler, 515 HPLC pump, In-Line Degasser AF, pump control module II, 2410 Refractive Index Detector (used for temperature control, not for detection), column heater module
Column: YMC-Triart C18, 3 mm×250 mm (manufactured by YMC Co., Ltd.) Mobile phase: liquid A: distilled water/acetonitrile/TFA=750/250/1
  liquid B: distilled water/acetonitrile/TFA=500/500/1
Detector: manufactured by Waters, 996 Photodiode Array Detector
Flow rate: 0.4 mL/min
Injection amount: 10 μL
Measurement wavelength range: 190 nm to 220 nm (result used was data at 205 nm)
Sample for analysis: aqueous solution containing about 120 ppm of main component peptide
(In the case of a raw material, the sample for analysis was obtained by dissolving the raw material in water to prepare an aqueous solution having the above-mentioned peptide concentration, and in the case of a composition, the sample for analysis was obtained by diluting the composition with water to prepare an aqueous solution having the above-mentioned peptide concentration.)
Software: Empower™2 (manufactured by Waters)

| Time (min) | A (%) | B (%) |
| --- | --- | --- |
| 0 | 100 | 0 |
| 35 | 60 | 40 |
| 65 | 0 | 100 |
| 70 | 0 | 100 |
| 70.01 | 100 | 0 |

With the use of software, the area and area percentage of the detected peak were calculated, and used as analysis results. In the analysis result, the area percentage was expressed to the second decimal place. On the basis of the analysis result, the content (%) of each of a main component peptide (peptide that was a synthesis target), a C-terminus-degraded product, and the other component (other than the main component peptide and the C-terminus-degraded product) was found out. The C-terminus-degraded product refers to a peptide having a carboxylic acid at its C-terminus produced by degradation of the amide group at the C-terminus of the main component peptide. Under the above-mentioned measurement conditions, the C-terminus-degraded product is generally detected at a slightly later retention time than that of the peak of the main component peptide. The increase amount of the content (%) of the C-terminus-degraded product in the composition was calculated by subtracting the content (%) of the C-terminus-degraded product in the raw material from the content (%) of the C-terminus-degraded product in the composition after storage (or after AC treatment).

[Visible Light Transmittance]
An absorbance was measured using Nano Drop 2000 (manufactured by Thermo Fisher Scientific), and a visible light transmittance was calculated on the basis of the result.

TABLE 2

| | Composition No. | AC treatment | Storage conditions Temperature [° C.] | Period [day(s)] | Substantial storage period [day(s)] |
| --- | --- | --- | --- | --- | --- |
| Example 1-1 | 1 | Present | Room temperature | 105 | 105 |
| Comparative Example 1-1 | C1 | Present | | | 105 |
| Example 3-1 | 3 | Present | | | 105 |
| Comparative Example 3-1 | C3 | Present | | | 105 |
| Example 1-2 | 1 | Present | 40 | 29 | 174 |
| Comparative Example 1-2 | C1 | Present | 40 | 29 | 174 |
| Example 2 | 2 | Present | 40 | 29 | 174 |
| Comparative Example 2 | C2 | Present | 40 | 30 | 180 |
| Example 3-2 | 3 | Present | 40 | 29 | 174 |
| Comparative Example 3-2 | C3 | Present | 40 | 29 | 174 |
| Example 4 | 4 | Present | 40 | 29 | 174 |
| Example 5 | 5 | Present | 40 | 30 | 180 |
| Example 6 | 6 | Absent | 40 | 28 | 168 |
| Example 7 | 7 | Present | 40 | 29 | 174 |
| Example 8 | 8 | Absent | 40 | 28 | 168 |
| Example 9 | 9 | Present | 40 | 28 | 168 |
| Comparative Example 4 | C4 | Present | 40 | 29 | 174 |
| Example 10 | 10 | Absent | 40 | 41 | 246 |
| Comparative Example 5 | C5 | Absent | 40 | 41 | 246 |
| Example 11 | 11 | Present | 40 | 30 | 180 |
| Comparative Example 6 | C6 | Present | 40 | 30 | 180 |
| Example 12 | 12 | Present | 40 | 30 | 180 |
| Comparative Example 7 | C7 | Present | 40 | 30 | 180 |
| Example 13 | 13 | Absent | 40 | 21 | 155 |
| | | | 60 | 0.6 | |
| Example 14 | 14 | Absent | 40 | 21 | 155 |
| | | | 60 | 0.6 | |
| Comparative Example 8 | C8 | Absent | 40 | 21 | 155 |
| | | | 60 | 0.6 | |
| Comparative Example 9 | C9 | Absent | — | — | — |
| Comparative Example 10 | C10 | Absent | — | — | — |

TABLE 3

| | Composition No. | Substantial storage period [days] | pH Before AC | pH After AC | pH After storage | Increase amount of content [%] of C-terminus-degraded product in peptide Increase amount after storage | Increase amount of content [%] of C-terminus-degraded product in peptide Increase amount due to AC | Light transmittance [%] Before storage | Light transmittance [%] After storage |
| --- | --- | --- | --- | --- | --- | --- | --- | --- | --- |
| Example 1-1 | 1 | 105 | 5.52 | 5.73 | 5.48 | 0.87 | 0.93 | 99 | 97 |
| Comparative Example 1-1 | C1 | 105 | 7.42 | 8.16 | 8.33 | 13.26 | 11.98 | 98 | 99 |

TABLE 3-continued

|  | Composition No. | Substantial storage period [days] | pH Before AC | pH After AC | pH After storage | Increase amount of content [%] of C-terminus-degraded product in peptide — Increase amount after storage | Increase amount due to AC | Light transmittance [%] Before storage | Light transmittance [%] After storage |
|---|---|---|---|---|---|---|---|---|---|
| Example 3-1 | 3 | 105 | 5.91 | 5.96 | 5.76 | 0.22 | 0.65 | 97 | 97 |
| Comparative Example 3-1 | C3 | 105 | 7.65 | 8.36 | 8.75 | 7.55 | 6.05 | 96 | 96 |
| Example 1-2 | 1 | 174 | 5.52 | 5.73 | 5.48 | 0.70 | 0.93 | 99 | 100 |
| Comparative Example 1-2 | C1 | 174 | 7.42 | 8.16 | 8.61 | 19.87 | 11.98 | 98 | 99 |
| Example 2 | 2 | 174 | 6.14 | 6.14 | 6.10 | 0.73 | 0.23 | 98 | 98 |
| Comparative Example 2 | C2 | 180 | 7.12 | 8.27 | 8.63 | 12.88 | 7.15 | 97 | 97 |
| Example 3-2 | 3 | 174 | 5.91 | 5.96 | 5.79 | 0.23 | 0.65 | 97 | 97 |
| Comparative Example 3-2 | C3 | 174 | 7.65 | 8.36 | 8.59 | 10.64 | 6.05 | 96 | 95 |
| Example 4 | 4 | 174 | 6.06 | 6.01 | 6.03 | 0.96 | 0.57 | 97 | 99 |
| Example 5 | 5 | 180 | 5.08 | 5.09 | 4.66 | 0.78 | 0.78 | 97 | 98 |
| Example 6 | 6 | 168 | 4.70 | — | 4.77 | 0.50 | — | 97 | 98 |
| Example 7 | 7 | 174 | 6.51 | 6.43 | 6.53 | 1.31 | 0.95 | 98 | 98 |
| Example 8 | 8 | 168 | 5.85 | — | 5.71 | −0.07 | — | 97 | 97 |
| Example 9 | 9 | 168 | 6.10 | 6.28 | 5.99 | 0.00 | 0.05 | 97 | 98 |
| Comparative Example 4 | C4 | 174 | 8.13 | 7.98 | 8.07 | 3.17 | 1.41 | 99 | 99 |

TABLE 4

|  | Composition No. | Substantial storage period [days] | pH Before AC | pH After AC | pH After storage | Increase amount of content [%] of C-terminus-degraded product in peptide — Increase amount after storage | Increase amount due to AC | Light transmittance [%] Before storage | Light transmittance [%] After storage |
|---|---|---|---|---|---|---|---|---|---|
| Example 10 | 10 | 246 | 5.51 | — | 5.53 | 0.25 | — | 99 | 99 |
| Comparative Example 5 | C5 | 246 | 6.94 | — | 8.71 | 5.71 | — | 99 | 98 |
| Example 11 | 11 | 180 | 5.54 | — | 5.59 | 1.33 | 0.82 | 99 | 98 |
| Comparative Example 6 | C6 | 180 | 7.12 | — | 8.59 | 8.82 | 7.79 | 96 | 95 |
| Example 12 | 12 | 180 | 5.73 | — | 5.70 | 0.43 | 0.04 | 96 | 96 |
| Comparative Example 7 | C7 | 180 | 7.22 | — | 8.53 | 11.64 | 7.40 | 97 | 97 |
| Example 13 | 13 | 155 | 5.51 | — | 5.99 | 0.14 | — | 98 | 99 |
| Example 14 | 14 | 155 | 4.56 | — | 4.78 | 0.35 | — | 99 | 99 |
| Comparative Example 8 | C8 | 155 | 7.42 | — | 8.41 | 13.87 | — | 98 | 98 |
| Comparative Example 9 | C9 | — | 5.29 | — | — | — | — | 19 | — |
| Comparative Example 10 | C10 | — | 5.39 | — | — | — | — | 69 | — |

The peptide compositions of Examples 1 to 14 each maintained its pH and transparency even when stored for a long period of time. The degradation of a peptide may occur during production, for example, during autoclave treatment of a composition, and during a storage period. In each of the compositions of Examples 1 to 14, the generation of the degradation product was suppressed even after storage of the composition. In each of the compositions of Examples 1 to 5, 7, 9, 11, and 12, the generation of the degradation product was suppressed even after AC treatment of the composition. In each of the peptide compositions of Examples, the increase amount of the content of the C-terminus-degraded product was 1.4% or less even after storage. Thus, each of the compositions obtained in Examples was considered to be capable of retaining the peptide during the storage period of a product in which the composition was expected to be used (e.g., 3 months to 1 year).

On the other hand, in the compositions of Comparative Examples, the contents of the C-terminus-degraded product after storage showed increases of 3% or more, among which there was even an increase of about 20%. Further, in each of the peptide compositions of Comparative Examples 1 to 4, 6, and 7, although the transparency was maintained, the content of the degradation product increased even after AC treatment of the composition. In addition, the peptide compositions of Comparative Example 9 and Comparative Example 10 were inferior in transparency (Comparative Example 9: 19%, Comparative Example 10: 69%). The peptide compositions of Comparative Examples 9 and 10 were inferior in transparency from before storage, and hence were not stored.

In addition, with regard to properties, Examples 1 to 14 were each a transparent gel, and maintained the state of the transparent gel even after storage. Comparative Examples 1 to 8 were each a transparent gel, and maintained the state of the transparent gel even after storage. Comparative Example 10 was a gel, and Comparative Example 9 was a liquid composition without forming a gel.

INDUSTRIAL APPLICABILITY

The peptide composition of the present invention can achieve both storage stability and desired characteristics. Accordingly, the peptide composition of the present invention can be suitably used in medical applications and the like.

The invention claimed is:

1. A peptide composition having a pH of from 4.5 to 6.6, the peptide composition comprising:
   a self-assembling peptide having a C-terminus comprising an amide group, wherein a total charge of amino acid residues contained in the self-assembling peptide is more than 0 and +3 or less, and an amino acid at the C-terminus of the self-assembling peptide comprises a basic amino acid;
   a buffering agent having a pKa of 3.5 or more and less than 7.5 and comprising histidine, thiamine nitrate, pyridine, bis-Tris, and/or N-methylmorpholine; and
   water.

2. The peptide composition according to claim 1, wherein the self-assembling peptide has the following amino acid sequence, with the amide group at the C-terminus:
   $a_1 b_1 c_1 b_2 a_2 b_3 d b_4 a_3 b_5 c_2 b_6 a_4$
   wherein:
   $a_1$ to $a_4$ each represent a basic amino acid residue,
   $b_1$ to $b_6$ each represent an uncharged polar amino acid residue and/or a hydrophobic amino acid residue, provided that at least five thereof each represent a hydrophobic amino acid residue,
   $c_1$ and $c_2$ each represent an acidic amino acid residue, and
   d represents a hydrophobic amino acid residue.

3. The peptide composition according to claim 2, wherein the amino acid sequence is selected from the group consisting of SEQ ID NOs: 1-4.

4. The peptide composition according to claim 1, wherein:
   a concentration of the buffering agent is in the range of from 1 mM to 100 mM, and
   a concentration of the self-assembling peptide is in the range of from 0.01 w/w % to 10 w/w %.

5. The peptide composition according to claim 4, wherein:
   a concentration of the buffering agent is in the range of from 5 mM to 43 mM, and
   a concentration of the self-assembling peptide is in the range of from 0.5 w/w % to 2.5 w/w %.

* * * * *